US010552954B2

(12) United States Patent
Beck

(10) Patent No.: US 10,552,954 B2
(45) Date of Patent: Feb. 4, 2020

(54) METHOD AND APPARATUS FOR GENERATION OF A PHYSIOLOGICALLY-DERIVED MAP CORRELATED WITH ANATOMICAL IMAGE DATA

(71) Applicant: Siemens Healthcare GmbH, Erlangen (DE)

(72) Inventor: Thomas Beck, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 248 days.

(21) Appl. No.: 15/727,970

(22) Filed: Oct. 9, 2017

(65) Prior Publication Data

US 2018/0101952 A1 Apr. 12, 2018

(30) Foreign Application Priority Data

Oct. 10, 2016 (DE) .................. 10 2016 219 607

(51) Int. Cl.
*G06T 7/00* (2017.01)
*G06T 11/00* (2006.01)

(52) U.S. Cl.
CPC .......... *G06T 7/0012* (2013.01); *G06T 11/001* (2013.01); *G06T 2200/24* (2013.01); *G06T 2207/10024* (2013.01); *G06T 2207/10088* (2013.01); *G06T 2207/30016* (2013.01); *G06T 2207/30101* (2013.01)

(58) Field of Classification Search
None
See application file for complete search history.

(56) References Cited

U.S. PATENT DOCUMENTS

| 4,649,482 A * | 3/1987 | Raviv ................... A61B 5/048 128/920 |
| 9,028,421 B2 * | 5/2015 | Fujii ................... A61B 3/1233 600/504 |
| 10,089,744 B2 * | 10/2018 | Stawiaski ............. A61B 6/481 |
| 10,089,960 B2 * | 10/2018 | Greenebaum ........... G09G 5/02 |

(Continued)

FOREIGN PATENT DOCUMENTS

| WO | WO-00/10454 A1 | 3/2000 |
| WO | WO-2010/115885 A1 | 10/2010 |

*Primary Examiner* — Anand P Bhatnagar
(74) *Attorney, Agent, or Firm* — Schiff Hardin LLP

(57) ABSTRACT

In a method and a computer for generating a physiologically-derived map correlated with anatomical image data spatially resolved physiologically-derived values within a value range are provided to a computer, as are anatomical image data. A frequency of occurrence of the provided physiologically-derived values is determined in the computer, depending on the occurrence of physiologically-derived values within the value range. A portion of the value range is selected in or via the computer, based on the determined frequency of the provided physiologically-derived values. Color coding is assigned in the computer to the physiologically-derived values of the value range outside the selected portion. A physiologically-derived map is generated by the computer by assigning a physiologically-derived value corresponding to the assigned color coding to its spatially resolved position in relation to the anatomical image data, and the map is shown at a display screen of the computer.

10 Claims, 2 Drawing Sheets

(56) References Cited

U.S. PATENT DOCUMENTS

| | | | |
|---|---|---|---|
| 10,275,908 B2 * | 4/2019 | Ishii | A61B 6/465 |
| 2003/0211036 A1 * | 11/2003 | Degani | A61B 5/0263 424/1.11 |
| 2004/0164983 A1 * | 8/2004 | Khozai | G06T 11/206 345/440 |
| 2006/0206012 A1 * | 9/2006 | Merrett | A61B 5/0205 600/300 |
| 2007/0232949 A1 * | 10/2007 | Saksena | A61B 5/044 600/515 |
| 2007/0299351 A1 * | 12/2007 | Harlev | A61B 5/0422 600/509 |
| 2007/0299352 A1 * | 12/2007 | Harlev | A61B 5/0422 600/509 |
| 2011/0319775 A1 * | 12/2011 | Fujii | A61B 3/1233 600/504 |
| 2015/0254419 A1 * | 9/2015 | Laughner | A61B 18/1492 703/11 |
| 2017/0316587 A1 * | 11/2017 | Ishii | A61B 6/465 |

\* cited by examiner

METHOD AND APPARATUS FOR GENERATION OF A PHYSIOLOGICALLY-DERIVED MAP CORRELATED WITH ANATOMICAL IMAGE DATA

BACKGROUND OF THE INVENTION

Field of the Invention

The present invention concerns a method, a computer, and an electronically readable data carrier for generating a physiologically-derived map correlated with anatomical image data.

Description of the Prior Art

In medical imaging, anatomical image data are typically generated by operation of a medical imaging apparatus, which shows a section of an examination object, in particular an examination area of the examination object. Anatomical image data show anatomy and/or pathology of the examination object such that a user can identify the structures of interest to the user based on the anatomical image data. The contrast and/or the resolution of the anatomical image data is defined by the type of medical imaging apparatus. Examples of such medical imaging apparatuses are computed tomography systems, magnetic resonance systems, positron emissions tomography (PET) systems, X-ray machines, and ultrasound devices.

Depending on the medical imaging apparatus, in addition to the anatomical image data, or instead of the anatomical image data, a physiologically-derived value that is characteristic of a physiological process of the examination object can be recorded. For example, the oxygenation of the blood can be measured using a magnetic resonance scanner. The measurement can be implemented in a spatially resolved manner. If the examination area includes at least a portion of the brain of the patient, then the measured, spatially resolved oxygenation of the blood can correspond to a spatially resolved activity of the brain. Therefore, spatially resolved physiologically-derived values, each indicating, for example, a measure for the oxygenation of the blood and/or the activity of the brain for a spatially resolved position, can be combined to form a map of the physiologically-derived characteristic.

SUMMARY OF THE INVENTION

An object of the invention is to provide a simple method for generating a map of such a physiologically-derived characteristic correlated with anatomical image data.

The method according to the invention for generating a physiologically-derived map correlated with anatomical image data includes the following steps. Spatially resolved physiologically-derived values, which are within a value range, are provided to a computer, as well as anatomical image data. A frequency of the provided physiologically-derived values is determined by the computer based on the physiologically-derived values within the value range. A portion of the value range is selected by the computer. Color coding is assigned by the computer to the physiologically-derived values of the value range outside the selected portion. The physiologically-derived map is generated by the computer by assigning a physiologically-derived value corresponding to the assigned color coding to its spatially resolved position in relation to the anatomical image data, and the map is shown at a display screen of the computer.

A spatially resolved physiologically-derived value is a physiologically-derived value that is representative of a position within the examination area. The position can be a point in space and/or a defined volume, in particular a voxel. A physiologically-derived value is preferably assigned to precisely one position. The physiologically-derived value characterizes a physiological process and/or physiological condition and/or a functionality of the examination object at the position assigned to the physiologically-derived value. The physiologically-derived value can be a quantitative value such as a flow rate and/or a diffusion rate of a liquid included in the examination object. The physiologically-derived value can be an absolute value, in particular a numerical value. The physiologically-derived value can be a relative value that, for example, indicates a physiological process and/or a physiological condition and/or a functionality at a position relative to a further physiologically-derived value at another position. A physiologically-derived value that is a relative value can be a numerical value. Several relative, numerical values can preferably be brought into relation with each other using a numerical scale. Relative values can optionally be indicated relative to a reference value. The reference value can be a physiologically-derived value at a defined position, for example. The physiologically-derived values can be based on the anatomical image data. The physiologically-derived values can be based on the medical data from which the anatomical image data can be reconstructed. The anatomical image data can be determined and/or generated regardless of the physiologically-derived values.

The provision of the spatially resolved physiologically-derived values to the computer designed to perform the method according to the invention preferably takes place by an algorithm that performs the inventive method accessing the spatially resolved physiologically-derived values. The spatially resolved physiologically-derived values can be stored in a memory of the computer.

The value range typically has a multiplicity of values, but at least two values, which values have the unit of a physiologically-derived value. The value range encompasses the physiologically-derived values assigned to the positions within the examination area. The value range is limited by a lower limit and by an upper limit, so the values between the lower limit and the upper limit are covered by the value range. The value range is a connected and/or continuous spatial area of the value range.

The physiologically-derived values are spatially resolved and are therefore each assigned to a certain position within the examination area. As an example, precisely five positions of the examination area can be assigned to the first physiologically-derived value. In this example, the first physiologically-derived value therefore occurs with a frequency of five in the examination area. By analogy, a frequency can be determined for each physiologically-derived value covered by the value range. Preferably, each physiologically-derived value covered by the value range is assigned a frequency with which this physiologically-derived value occurs within the examination area. The frequency can also be determined together for at least two adjacent physiologically-derived values, with which frequency the at least two adjacent physiologically-derived values within the examination area occur. Compared to the value range, the frequency can be as discretized (divided) or more discretized, than the value range. For determining the frequency of the provided physiologically-derived values, a histogram can be generated, the histogram indicating a distribution of the frequency of the physiologically-derived values as a function of the value range.

The frequency of the physiologically-derived values covered by the value range may also relate to an additional area, which is different from the examination area. The additional area is a portion of the examination area and may be specified by a mask, for example. The additional area is obtained, for example, by the intersection of the mask with the examination area or by the complement of the mask in relation to the examination area. The mask may be, for example, a certain structure and/or pathology that should not be considered in general, or should be considered only when determining the frequency of the physiologically-derived values. The mask may be, for example, all those positions that have a prescribed physiologically-derived value. The mask may include, for example, all those positions at which the physiologically-derived values and/or the anatomical image data are of a particularly low or high quality. The quality can correlate, for example, with noise and/or a signal-to-noise ratio. If, for example, the physiologically-derived values indicate a correlation of an activity of the brain at rest, the additional area may include the seed region required for determination of the correlation. The additional area can be determined automatically. The additional area can also be selected by a user.

The portion of the value range that is selected in the context of the method according to the invention is typically a section of the value range. The portion thus is preferably a connected spatial area. This area is typically a section of the value range that starts above the lower limit of the value range and ends below the upper limit of the value range, such that the area of the portion typically does not include the lower limit and the upper limit and/or is limited by the lower limit and the upper limit. The area of the portion is designed such that the value range is divided into three parts by selecting the area, wherein a first part of the value range is covered only by the value range, a second part of the value range is covered by the value range and by the area of the portion, and a third part of the value range is covered only by the value range. Two or more areas of the value range may also be selected.

Color coding typically involves colors of a color space, which are differentiated according to a scale. Precisely one color of the color space is assigned to one position of the scale. Such color coding can be assigned to the value range such that the area of the selected portion is excluded. If the selection of the portion subdivides the value range as described above into a first part and a second part and a third part, the scale can thus be divided into two areas, wherein a first area of the scale is assigned to the first part of the value range and a second area of the scale to the third part of the value range. Color coding of various color spaces can also be assigned to the first part of the value range and the third part of the value range. The color space can be, for example, the RGB color space, the HSV color space, the CMYK color space, or a gray scale. The color space can be individually defined. The color space can be individually determined, if necessary, by interpolation. According to such an assignment of the color coding to the value range, precisely one color can be assigned to each physiologically-derived value that is outside the selected portion and is covered by the value range.

A physiologically-derived value is assigned to a first position of the examination area. If the first physiologically-derived value is covered by the value range but not by the selected portion, a color that can also be assigned to the first position is assigned to the first physiologically-derived value. A second physiologically-derived value is assigned to a second position of the examination area. If the second physiologically-derived value is covered by the value range and by the selected portion, then no color is assigned to the second physiologically-derived value. In addition, spatially resolved anatomical image data are typically available for the examination area. Typically, at least one first pixel of the anatomical image data can be assigned to the first position and at least one second pixel of the anatomical image data to the second position. As noted, the anatomical image data are made available to the computer in order to execute the method according to the invention.

According to this approach, a color, or no color, can be assigned to the positions covered by the examination area, taking into account the corresponding physiologically-derived values, the selected portion, and the color coding, so a spatial distribution of the colors covered by the color coding is generated. This spatial distribution can be the physiologically-derived map. Physiologically-derived values to which no color was assigned appear colorless in the color card.

In addition, at least one pixel of the anatomical image data can be assigned to each position. Thereby, the physiologically-derived map and the anatomical image data for the examination area are able to be linked, in particular spatially linked. The anatomical image data can be shown with the physiologically-derived map superimposed thereon. Anatomical image data are typically shown as monochrome images, whereas the physiologically-derived map is preferably in color. According to the selection of the portion of the value range, there are positions of the examination area at which the physiologically-derived map is colorless, whereas anatomical image data for these positions is available.

An advantage of this method is that the physiologically-derived map can be generated particularly easily. A physiological process and/or a physiological condition and/or a functionality of the examination object is typically determined using the generated physiologically-derived map, preferably in combination with the anatomical image data. When the physiologically-derived map according to the inventive method is generated, focusing on relevant physiologically-derived values is facilitated. For a diagnosis, irrelevant physiologically-derived values can be suppressed by selecting the portion, and thus excluded from the physiologically-derived map. The portion can be selected such that positions and/or structures of the examination area of interest for a diagnosis are marked in color. In the physiologically-derived map, colorless positions and/or structures are typically of no particularly great significance for the desired diagnosis. At these colorless positions, the anatomy of the examination area can be shown with a representation of the anatomical image data superimposed with the physiologically-derived map, facilitating a diagnosis and/or an assignment of the color-coded physiologically-derived values to anatomy. A physiologically-derived map can thus be specially tailored to the subjective requirements of a user. Particularly interesting physiologically-derived values can be highlighted and/or represented particularly accurately in a physiologically-derived map generated in the method according to the invention, thus enabling a particularly good diagnosis. If the selected portion were not excluded in the assignment of the color coding to the physiologically-derived values, then the color coding would have to be assigned to the entire value range, thus reducing the resolution of the color coding. The exclusion of the selected portion in the assignment of the color coding to the physiologically-derived values thus enables a higher resolution of the color coding, so smaller differences in the generated physiologically-derived map are easier to detect. The physiologically-derived map is generated so that it can be shown with the image data by a well-defined superimposition. A user-specific representation is possible, enabling a particularly precise diagnosis.

In an embodiment of the method, the selection of the portion of the value range is based on the frequency of the provided physiologically-derived values. Therefore, the frequency of the provided physiologically-derived values is taken into consideration when selecting the portion.

For example, the portion can be selected such that the physiologically-derived values that occur with particular frequency are covered by the selected portion. Therefore, no color is assigned to these physiologically-derived values in the color coding, for which reason they are colorless in the physiologically-derived map, and consequently not represented. Physiologically-derived values that, for example, are in the second part of the value range, occur more frequently than physiologically-derived values in a border area of the value range, hence, for example, in the first part and/or the third part of the value range. Typically, the border areas of the value range are diagnostically relevant because they may characterize rarely occurring and/or explicitly induced processes and/or conditions, for example. Thus, physiologically-derived values that occur less frequently but characterize processes and/or conditions of particularly special statistical significance can be highlighted with the selection of the portion based on the frequency of the provided physiologically-derived values. For certain physiological processes and/or conditions, for example, the detection of rare physiologically-derived values is relevant, which is why a selection of the portion based on the frequency of the physiologically-derived values is particularly advantageous. Depending on a clinical situation, it may be necessary to detect such processes and/or conditions and/or based thereon, in order to make a diagnosis, such as to examine the functionality of an organ. Having excluded particularly frequent physiologically-derived values from the physiologically-derived map, the rarely occurring physiologically-derived values can be shown in a higher resolution of color coding, so minor differences in the rarely occurring physiologically-derived values can be better visualized, and the diagnosis can be made more easily. Moreover, based on the frequency, physiologically-derived values of the value range that do not assume any and/or only very few positions of the examination area are excluded. Statistical noise of the physiologically-derived values thus can be suppressed.

In general, the frequency of the provided physiologically-derived values is an important indicator of the relevance of certain physiologically-derived values. Knowledge of the frequency of a physiologically-derived value and consideration of the frequency when selecting the portion of the value range makes it possible to select the physiologically-derived values to be shown in the physiologically-derived map with particular precision. The selection can be individually tailored to a user. The frequency of the provided physiologically-derived values is an important indicator that allows the relevance of certain physiologically-derived values to be estimated with particular precision. The quality of the physiologically-derived map thus can be improved.

In an embodiment of the method, the selection of the portion of the value range is made based on a threshold value, and/or the significance for the frequency of the provided physiologically-derived values is done as a function of the physiologically-derived values within the value range. Statistical means this can be employed to select the portion based on the frequency of the provided physiologically-derived values. The threshold value and/or the significance is preferably predetermined.

The selection of the portion of the value range can be done such that the selected portion has physiologically-derived values with a relative frequency lower and/or higher than a defined threshold value. The relative frequency preferably indicates the frequency of a physiologically-derived value in relation to the frequency of the most frequently occurring physiologically-derived value. The selection of the portion can take place such that the physiologically-derived values covered by the selected portion have a defined significance. The significance determines a proportion of the most frequently occurring physiologically-derived values of all the physiologically-derived values covered by the value range. Such a significance can be 95% or 99%, for example. Those physiologically-derived values which occur particularly frequently thus can be excluded from the physiologically-derived map.

Such a selection of the portion preferably takes place automatically. This selection of the portion can be performed in a very robust, standardized and reproducible manner, so the physiologically-derived map can be generated particularly easily. This is advantageous for the first generation of a physiologically-derived map based on the physiologically-derived values, because typically the physiologically-derived values and/or the frequency of the physiologically-derived values are individualized for each examination object. The user who makes a diagnosis based on the physiologically-derived map and/or the anatomical image data, receives an initial impression of the physiologically-derived values and their spatial distribution, by the generated physiologically-derived map. The threshold value and/or the significance can preferably be changed such that the physiologically-derived values covered by the physiologically-derived map can be interactively and individually adjusted to the examination object and/or the type of examination and/or the physiologically-derived values and/or the requirements of a user who evaluates the physiologically-derived map.

In another embodiment of the method, the assignment of the color coding includes a specification of a transparency for the color coding. This embodiment is particularly advantageous when the anatomical image data and the physiologically-derived map are shown. The physiologically-derived map is preferably linked to the anatomical image data such that both can be displayed superimposed in one image. The physiologically-derived map is typically colorless at some positions, whereas the anatomical image data has one pixel at all the positions covered by the examination area. It is therefore advantageous to use the anatomical image data as a background image and to superimpose the physiologically-derived map on the anatomical image data. It can be advantageous to detect the anatomy behind the colors of the physiologically-derived map despite the superimposed physiologically-derived map. For this purpose, a transparency can be prescribed for the physiologically-derived map such that the anatomical image data superimposed by the physiologically-derived map can also be detected at the same time as the physiologically-derived map at the positions at which the physiologically-derived map is not colorless.

The maximum transparency is preferably characterized by the physiologically-derived map being colorless at all the positions covered by the examination area. The minimum transparency is preferably characterized by, at positions at which the physiologically-derived map is not colorless, no anatomical image data being discernible. A transparency between the minimum transparency and the maximum transparency is selected. Different parts of the value range may be shown with different transparencies. Thus, for example, the first part of the value range may have a transparency of 0.7, and the second part of the value range a transparency of 0.2.

An advantage of this embodiment is that, by selecting the transparency appropriately, the anatomical image data are visible despite the superimposed physiologically-derived map. By such a superimposed representation, the physiologically-derived map can be shown in a manner that is particularly easy to understand. A region of the examination area which is highlighted by the color coding can be identified particularly well, because the anatomical image data indicate anatomy and/or a pathology within the examination area with good precision, in particular in higher resolution. This enables a precise assignment of the region to the corresponding anatomy and a precise diagnosis. The user preferably selects the type of underlying anatomical image data, in particular its contrast. As a result, evaluation can take place robustly and individually for a user.

In another embodiment of the method, the selection of the portion of the value range and/or the determination of the transparency is/are done via an interaction element. A user who monitors and/or executes the performance of the method according to the invention using the computer can therefore specify the portion and/or adjust a previously determined portion to the user's requirements. The user can specify the transparency with which the physiologically-derived map is superimposed on the anatomical image data and/or adjust it to the user's requirements. For this purpose, the computer has a user interface that enables such an interaction by the user. The interaction element can be, for example, a text field, a slide control, or an arrow. The interaction element is preferably designed such that it is shown on a display screen of the user interface. The user preferably operates the interaction element with an input unit of the user interface, for example, enter a text in a text field, move a slide control in at least one direction or change a value by operating an arrow. Thus a value can be specified for the transparency and/or for a limit of the selected portion.

The selection of the portion of the value range and/or the determination of the transparency with the interaction element preferably takes place interactively. Preferably, the user is shown the corresponding change in the physiologically-derived map and/or in the anatomical image data immediately after the activation of the interaction element. The user thus receives real-time feedback.

An advantage of this embodiment is that the physiologically-derived map correlated with anatomical image data can be presented particularly flexibly and can be easily adjusted to the requirements of the user. The interaction element enables the interactive alteration of a representation of the physiologically-derived map and/or the anatomical image data, so the representations can be changed particularly quickly and intuitively.

In another embodiment of the method, the generation of the physiologically-derived map is a representation of the physiologically-derived map superimposed on the anatomical image data according to the assigned color coding in at least two different orientations. The anatomical image data are preferably three-dimensional such that the anatomical image data divide the examination area into sub-areas, called voxels. One orientation preferably shows a cross-section through the examination area an. One orientation can also be a curved cross-section through the anatomical image data, which is preferably three-dimensional. One orientation may also be a cross-section through the anatomical image data in a perspective view, wherein according to the perspective visible areas of the examination area can be shown outside the cross-section. If the physiologically-derived map and the anatomical image data are shown in at least two different orientations, the user can then view the examination area from different perspectives. Thereby, for one position the physiologically-derived map and the anatomical image data can be shown at the same time from different perspectives, so the user obtains a better overview of the anatomy and/or pathology, combined with the physiologically-derived map. In this way, a more reliable diagnosis can be made.

In an embodiment of the method, the anatomical image data have a resolution that differs from the resolution of the physiologically-derived map. Typically, the anatomical image data have a higher resolution than the physiologically-derived map. For the determination and/or generation of a physiologically-derived value, an image of medical data is required. The medical data are typically recorded with a medical imaging scanner and the physiologically-derived values are typically determined and/or generated on the basis of the medical data. Such medical data can also be reconstructed to form medical image data. In the context of the inventive method, the medical image data can be used as the anatomical image data on which the physiologically-derived map is superimposed. Alternatively, anatomical image data reconstructed from additional medical data, and which differ from the medical image data, can be used.

Anatomical image data can be two-dimensional or three-dimensional. Anatomical image data can show anatomy and/or pathology of the examination object. Anatomical image data can show a function of the examination object in a spatially resolved manner. If, for example, a magnetic resonance scanner is used to generate the anatomical image data, then the anatomical image data can be magnetic resonance data that represent a diffusion map, an ADC map, and/or a perfusion map, and/or can be functional image data. The anatomical image data can also be medical data. The additional medical data can also be recorded with a medical imaging apparatus other than the apparatus for the recording of medical data. The additional medical data and/or the anatomical image data can be made available to the computer that implements the method according to the invention.

The resolution of anatomical image data and/or the physiologically-derived map is defined by the space between two adjacent pixels and/or positions. Typically, the anatomical image data differs from the medical image data, wherein it preferably has a higher resolution than the medical image data. The recording of the medical data that are used to generate the physiologically-derived values is complex, and for magnetic resonance scans, depending on the type of physiologically-derived values, takes longer than average. Therefore, such medical data are typically recorded in a lower spatial resolution, such that the anatomy in such medical image data is only imprecisely reproduced. The physiologically-derived map that reproduces such physiologically-derived values, however, has sufficient resolution so as to permit detection of areas of particular physiologically-derived values. If the physiologically-derived map is shown with the anatomical image data superimposed and the anatomical image data have a higher resolution than the physiologically-derived map, areas of particular physiologically-derived values can be identified easily because anatomy and/or pathology within the examination area is nevertheless shown in higher resolution. This enables a precise assignment of a color-marked position on the corresponding anatomy. The user can select the type of underlying anatomical image data, in particular its contrast. As a result, the evaluation can take place robustly and individually for a user.

In an embodiment of the method, the physiologically-derived values indicate a correlation of the spatially resolved positions with a seed region, and the generation of the physiologically-derived map includes a definition of the seed region, a correlation analysis taking into account the seed region and medical data, and the generation of spatially resolved physiologically-derived values based on the correlation analysis.

The physiologically-derived values are preferably based on medical data recorded by a magnetic resonance scanner. The medical data are preferably time-resolved. Preferably the medical data are recorded using a method for functional magnetic resonance imaging, in particular a resting-state method. The seed region is preferably defined on the basis of medical image data and/or anatomical image data, so the user is shown the medical image data and/or the anatomical image data on a display screen. The user can indicate a seed region via an input unit based on the image data shown. The seed region is indicated by selecting at least one pixel of the image data shown. The seed region includes at least one pixel of the image data shown. Preferably the seed region has several spatially linked pixels of the image data shown. The seed region is preferably a portion of the examination area. The seed region can be selected automatically. For example, an algorithm based on the medical image data and/or anatomical image data can detect a seed point and/or a seed region.

A correlation analysis is preferably implemented in order to determine at least one portion of the examination area that is active at the same time as a seed region from a chronological point of view. For this purpose, a time-resolved and spatially resolved oxygenation of the blood, which can be determined on the basis of the medical data, is analyzed. A correlation analysis is performed on the basis of seed points. Spatially and temporally resolved changes in intensity of the signal in temporally resolved image data are analyzed. These changes in intensity are caused by a change in the oxygenation of the blood. A respective correlation of the changes in intensity relative to a change in the intensity of the seed region is determined for the pixels of the examination area. The correlation is a temporal correlation. The spatially resolved physiologically-derived values are preferably a measure of the relative strength of the correlation of a position with the seed region.

An advantage of this embodiment is that functional magnetic resonance data can be evaluated particularly easily and comprehensively. The method allows a complete analysis to be performed on the basis of the medical data. This is advantageous for physiologically-derived values that indicate a correlation with a seed region as the performance of the correlation analysis and the procedural steps necessary prior to this are cumbersome. The procedural steps necessary for the correlation analysis are performed regardless of the generation of the medical data, in an arithmetic unit independent of the medical imaging apparatus. In this embodiment of the method, in the generation of the physiologically-derived map, the computer also performs the evaluation of the medical data, in particular the correlation analysis. This enables a continuous workflow and thus reduces the period for the generation of a physiologically-derived map.

In an embodiment of the method, the physiologically-derived values indicate a correlation of the spatially resolved positions with a seed region. The spatially resolved physiologically-derived values are therefore preferably a measure of the relative strength of the correlation of a position with the seed region. Such physiologically-derived values can be made available to the method, such as by having been generated previously. The generation can have been implemented according to the aforementioned embodiment. An advantage of this embodiment is that the method can also be applied to previously generated physiologically-derived values. Various quantities with physiologically-derived values that were recorded with various medical imaging apparatuses and/or for various examination objects can be made available to the method such that the method according to the invention is independent of the medical imaging apparatus used for generating the physiologically-derived values.

Furthermore, the invention encompasses a computer with a user interface and an arithmetic unit, which is designed to generate a physiologically-derived map correlated with anatomical image data. For this purpose, the user interface of the computer has a display screen that can show the physiologically-derived map correlated with anatomical image data and/or can display the frequency of the provided physiologically-derived values, depending on the occurrence physiologically-derived values within the value range. The user interface has an input unit such via which selection of a portion of the value range can be made. The arithmetic unit is configured to assign a color coding to the physiologically-derived values of the value range outside the selected portion and/or to generate the physiologically-derived map by assigning a physiologically-derived value corresponding to the assigned color coding to its spatially resolved position in relation to the anatomical image data. The arithmetic unit can be configured to make available spatially resolved physiologically-derived values that are within a value range, and/or to determine the frequency of the provided physiologically-derived values depending on the occurrence physiologically-derived values within the value range. The arithmetic unit can be configured to select the portion of the value range.

Embodiments of the computer according to the invention are analogous to the embodiments of the method according to the invention. The computer can have additional control components that are necessary or advantageous for performing the method according to the invention. Computer programs and additional software by which the processor of the computer automatically controls and/or executes the method according to the invention can be saved in a memory of the computer.

The present invention also encompasses a non-transitory, computer-readable data storage medium encoded with programming instructions (program code) that, when the storage medium is loaded into a computer, cause the computer to implement any or all embodiments of the method according to the invention as described above.

DESCRIPTION OF THE PREFERRED EMBODIMENTS

Figure 1:
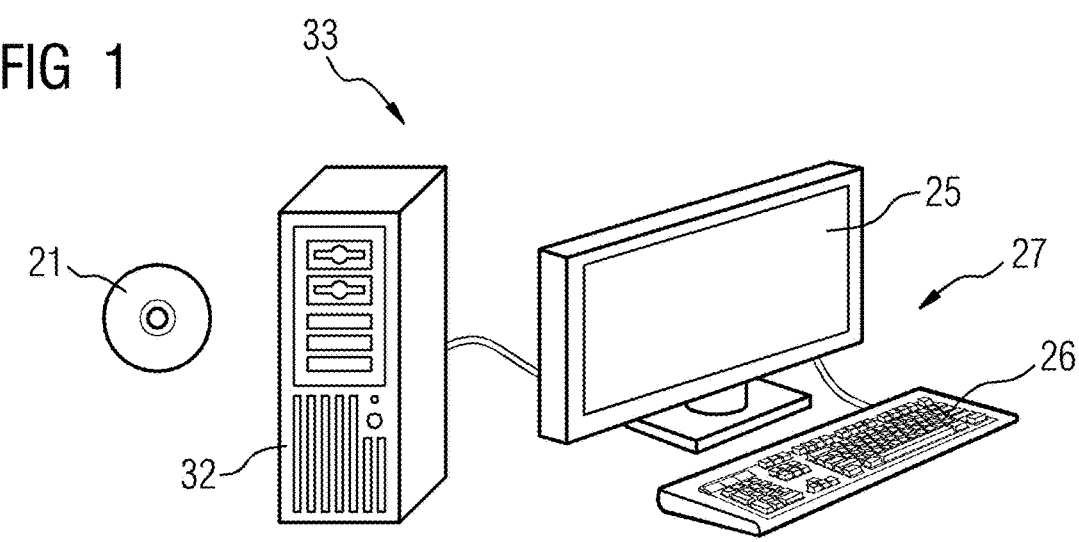
FIG. 1 schematically illustrates a computer according to the invention.

FIG. 1 shows a computer 33 according to the invention in a schematic illustration. The computer 33 has an arithmetic unit (processor) 32 that is designed (configured) to perform the method according to the invention for generating a physiologically-derived map correlated with anatomical image data. The computer 33 has a user interface 27. The arithmetic unit 32 is preferably connected to the user interface 27. The user interface 27 has a display screen 25 and an input unit 26. The user interface 27 enables the interaction of a user with the arithmetic unit 32 and thus with the computer 33. The frequency of occurrence of the provided physiologically-derived values within the value range 12 (see FIG. 3) and/or a generated physiologically-derived map can be displayed for a user at the display screen 25, for example, on at least one monitor thereof. Via the input unit 26, a portion 10 and/or a transparency can be selected by the use of an interaction element that is shown on the display screen 25.

The computer 33 is designed to perform the inventive method for generating a physiologically-derived map correlated with anatomical image data. For this purpose, the computer 33 has computer programs and/or software that can be loaded directly into the arithmetic unit 32 of the computer 33, with program resources to perform the inventive method for the evaluation of medical data with a time resolution when the computer programs and/or software are executed in the computer 33. To this end, the arithmetic unit 32 has a processor designed to execute the computer programs and/or software. The computer 33 is thus designed to perform the inventive method according to the invention. Alternatively, the computer programs and/or software can also be stored on an electronically readable data carrier (storage medium) 21 separate from the computer 33, which can be loaded into the computer 33.

The computer 33 can be integrated into a medical imaging apparatus. The computer 33 can also be installed separately from the medical imaging apparatus. The computer 33 can be connected to the medical imaging apparatus. The computer 33, in particular the arithmetic unit 32, may have additional components that are common to processors. The general functioning of the arithmetic unit 32 (other than performance of the inventive method) is known to those skilled in the art, such that a detailed description of such additional components is not necessary herein.

The inventive method for generating a physiologically-derived map correlated with anatomical image data may be in the form of computer code that causes the computer 33 to implement the method. The code is stored on an electronically readable data carrier 21 that can be loaded into the computer 33.

Figure 2:
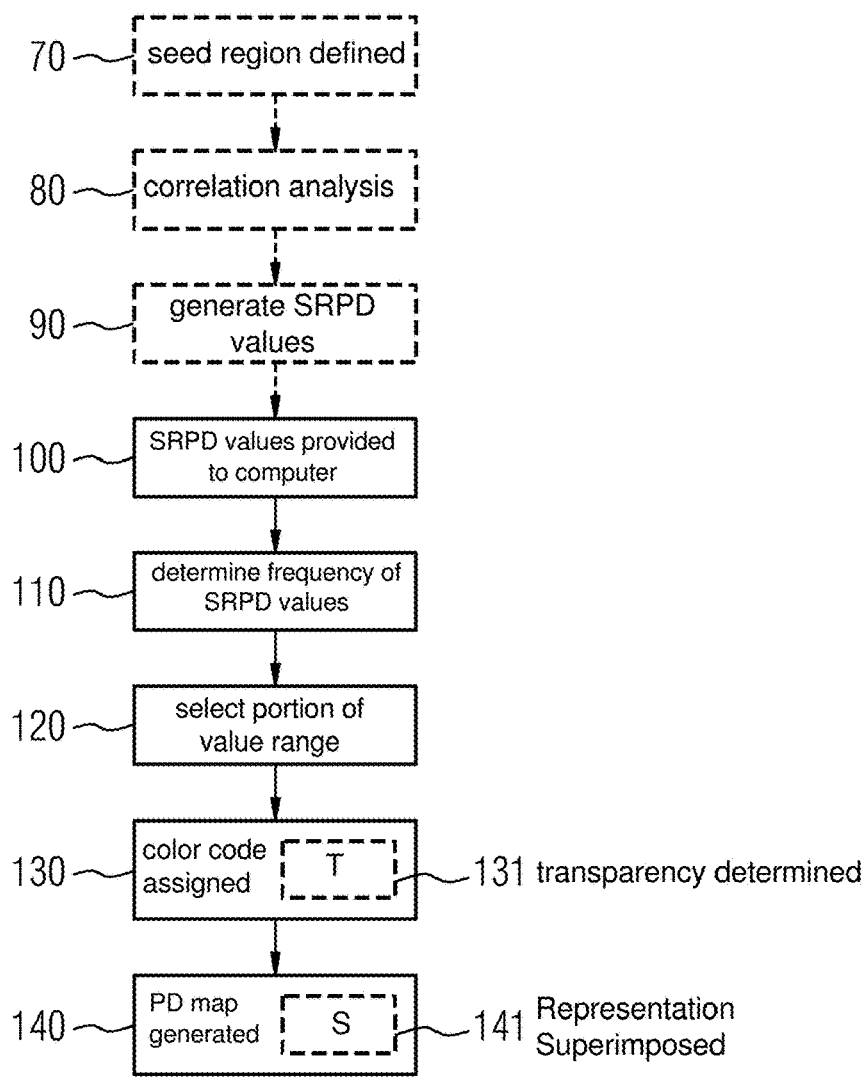
FIG. 2 is a flowchart of an embodiment of the method according to the invention.

FIG. 2 shows a flowchart of an embodiment of the method according to the invention for generating a physiologically-derived map correlated with anatomical image data. The method is performable by the computer 33. At the beginning of the method, in step 100, spatially resolved physiologically-derived values, which are within a value range 12, are made available to the computer 33, as are anatomical image data. The anatomical image data may already be stored in the computer 33. In step 110, a frequency of the provided physiologically-derived values is determined, depending on the occurrence of the physiologically-derived values within the value range 12. The determination of the frequency takes place in the arithmetic unit 32. In the following step 120, a selection of a portion 10 of the value range 12 takes place.

The selection of the portion 10 in step 120 can take place on the basis of the frequency of the provided physiologically-derived values. The selection of the portion 10 in step 120 can take place on the basis of a threshold value and/or a significance for the frequency of the provided physiologically-derived values, depending on the physiologically-derived values within the value range 12. In step 130, a color coding 14 is assigned to the physiologically-derived values of the value range 12 outside the portion 10. The assignment of the color coding 14 may optionally be a further step 131, by specification of a transparency for the color coding 14. The selection of the portion 10 in the step 120 and/or the determination of the transparency in step 131 can take place with the use of an interaction element. Such an interaction element is shown on the display screen 25 and the interaction element is operated via the input unit 26. In step 140, the physiologically-derived map is generated by assigning a physiologically-derived value corresponding to the assigned color coding 14 to its spatially resolved position in relation to the anatomical image data. The generation of the physiologically-derived map may optionally comprise the procedural step 141, a representation superimposed on the anatomical image data of the physiologically-derived map corresponding to the assigned color coding 14 in at least two different orientations.

In order to generate the physiologically-derived map correlated with anatomical image data according to steps 100, 110, 120, 130, 140, the spatially resolved physiologically-derived values can be provided in step 100 by generating those values. For this purpose, a definition of a seed region 15 can take place in step 70. In the following step 80, a correlation analysis is performed, taking into account the seed region 15 and medical data. In step 90, spatially resolved physiologically-derived values are generated on the basis of this correlation analysis. According to this embodiment, the physiologically-derived values represent a correlation of the spatially resolved positions with the seed region 15.

Figure 3:
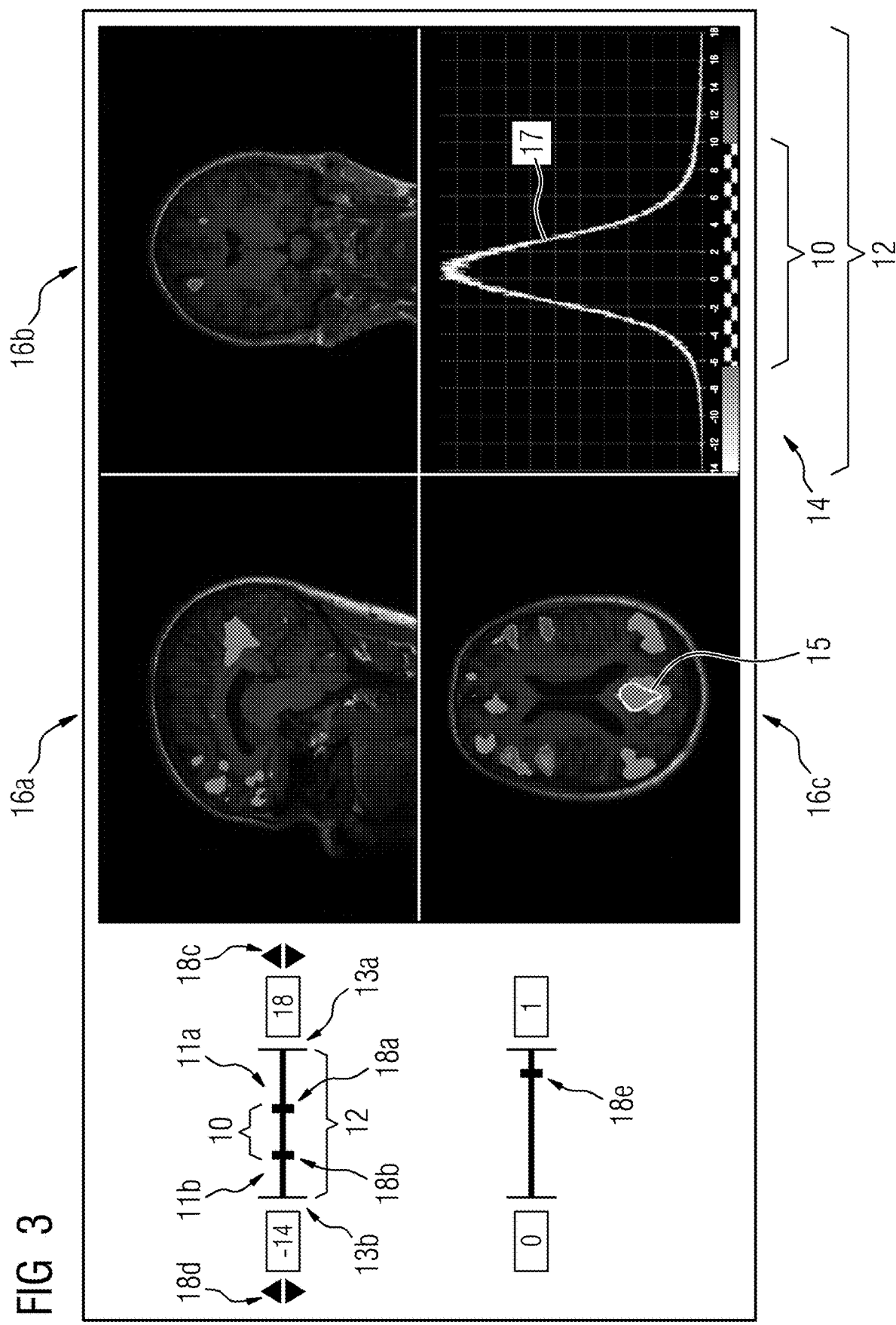
FIG. 3 shows an exemplary embodiment for color coding assigned to a value range with a generated physiologically-derived map in accordance with the invention.

FIG. 3 shows an exemplary embodiment of a color coding 14 assigned to a value range 12 with a generated physiologically-derived map which is shown superimposed on anatomical image data. The representation takes place on the display screen 25, wherein interactions, for example, the selection of the portion 10, can take place between a user and the computer 33 via the input unit 26 and the display screen 25. The physiologically-derived values on which the physiologically-derived map is based indicate the correlation of the spatially resolved positions with the seed region 15. The anatomical image data and the physiologically-derived map superimposed on the anatomical image data are three-dimensional and are displayed in three different orientations. Thus, in this exemplary embodiment, a sagittal representation of the anatomical image data is superimposed with the physiologically-derived map 16a, a coronal representation of the anatomical image data is superimposed with the physiologically-derived map 16b and a transverse representation of the anatomical image data is superimposed with the physiologically-derived map 16c. The anatomical image data has a higher resolution than the physiologically-derived map. If necessary, the seed region 15 can be defined and/or changed on the basis of the anatomical image data, whereupon the correlation analysis can be performed taking into account the seed region 15 and first-time or altered spatially resolved physiologically-derived values generated. In addition, the frequency of the provided physiologically-derived values 17 is shown depending on the occurrence of the physiologically-derived values within the value range 12. This is typically shown as a graph, wherein the value range 12 is the abscissa.

The portion 10 of the value range 12 can be selected and a color coding 14 assigned to the physiologically-derived values of the value range 12 outside the portion 10. The portion 10 can be selected via a first interaction element 18a and a second interaction element 18b. An upper limit 11a of the portion 10 can be determined with the first interaction element 18a, for example, a slide control, and a lower limit 11b of the portion 10 with the second interaction element 18a, for example, a slide control. The section of the value range 12 between the lower limit 11b and the upper limit 11a corresponds to the portion 10. In this example, the lower limit 11b is determined by the value "−6.4" and the upper limit 11a by the value "10". Preferably, the value range 12 can also be selected via a third interaction element 18c and a fourth interaction element 18d. An upper limit 13a of the value range 12 can be determined with the third interaction element 18c, for example, a text field and/or an interactive arrow, and a lower limit 13b of the value range 12 with the fourth interaction element 18d, for example, a text field and/or an interactive arrow. The section between the lower limit 13b and the upper limit 13a corresponds to the totality of the value range 12. In this example, the lower limit 13b is determined by the value "−14" and the upper limit 11a is determined by the value "18". The interaction elements necessary for the selection of the portion 10 and/or the value range 12 can also be shown at the abscissa that indicates the value range 12 in the representation of the frequency of the provided physiologically-derived values 17, or can be integrated into this presentation.

In addition, a transparency can be designated for the color coding 14. This can be done via a fifth interaction element 18e, for example, a slide rule (scale). The transparency can be defined by a value between "0" (physiologically-derived map not visible) and "1" (at the spatially resolved positions at which an physiologically-derived value is located outside the portion 10, the anatomical image data is completely superimposed by the physiologically-derived map, hence, no longer visible). The interaction elements 18a, 18b, 18c, 18d, 18e can be operated using the input unit 26.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a physiologically-derived map correlated with anatomical image data, comprising:
   providing spatially resolved physiologically-derived values to a computer, which are within a value range, and providing anatomical image data to the computer;
   in said computer, determining a frequency of occurrence of said values within said value range;
   in or through said computer, selecting a portion of said value range based on said frequency of occurrence of the values;
   in said computer, assigning color coding to values of the value range outside of the selected portion;
   in said computer, generating a map that correlates said values with said anatomical image data by assigning a value, according to the assigned color coding thereof, to a spatially resolved position of that value in relation to the anatomical image data; and
   presenting said map at a display screen in communication with said computer.

2. A method as claimed in claim 1 comprising selecting said portion of said value range on at least one basis selected from the group consisting of a threshold value, and a significance of the respective frequency of occurrence of the values.

3. A method as claimed in claim 1 comprising assigning said color coding by specifying a transparency for said color coding.

4. A method as claimed in claim 3 comprising selecting said transparency via an interaction element operable by a user of said computer.

5. A method as claimed in claim 1 comprising selecting said portion by an interaction element operable by a user of the computer.

6. A method as claimed in claim 1 comprising generating said map as a representation of said values with the assigned color coding superimposed on said anatomical image data, in at least two different orientations.

7. A method as claimed in claim 1 comprising generating said map so as to have a resolution that differs from a resolution of said anatomical image data.

8. A method as claimed in claim 1 comprising generating said map by:
   defining a seed region;
   executing a correlation analysis dependent on said seed region and medical data; and
   generating spatially resolved generated values based on said correlation analysis, said generated values designating a correlation with said seed region.

9. A computer comprising:
   a user interface and a processor;
   said processor being configured to receive, via said user interface, spatially resolved physiologically-derived values, which are within a value range, to receive anatomical image data;
   said processor being configured to determine a frequency of occurrence of said values within said value range;
   said processor being configured to said select a portion of said value range based on said frequency of occurrence of the values;
   said processor being configured to assign color coding to values of the value range outside of the selected portion;
   said processor being configured to generate a map that correlates said values with said anatomical image data by assigning a value, according to the assigned color coding thereof, to a spatially resolved position of that value in relation to the anatomical image data; and
   said processor being configured to present said map at a display screen of said user interface.

10. A non-transitory, computer-readable data storage medium encoded with programming instructions, said storage medium being loaded into a computer and said programming instructions causing said computer to:
    receive spatially resolved physiologically-derived values, which are within a value range, and to receive or access anatomical image data;
    determine a frequency of occurrence of said values within said value range;
    select a portion of said value range based on said frequency of occurrence of the values;
    assign color coding to values of the value range outside of the selected portion;
    generate a map that correlates said values with said anatomical image data by assigning a value, according to the assigned color coding thereof, to a spatially resolved position of that value in relation to the anatomical image data; and present said map at a display screen in communication with said computer.

\* \* \* \* \*